United States Patent [19]

Anderson

[11] Patent Number: 4,666,942

[45] Date of Patent: May 19, 1987

[54] PESTICIDAL BENZOYLUREA COMPOUNDS

[75] Inventor: Martin Anderson, Whitstable, England

[73] Assignee: E. I. Du Pont de Nemours and Company, Wilmington, Del.

[21] Appl. No.: 889,523

[22] Filed: Jul. 24, 1986

Related U.S. Application Data

[62] Division of Ser. No. 719,791, Apr. 4, 1985.

[30] Foreign Application Priority Data

Apr. 10, 1984 [GB] United Kingdom ............... 8409240
Aug. 17, 1984 [GB] United Kingdom ............... 8420930

[51] Int. Cl.[4] .................................. A01N 47/28
[52] U.S. Cl. .................................. 514/594
[58] Field of Search ............................ 514/594

[56] References Cited

U.S. PATENT DOCUMENTS

| | | | |
|---|---|---|---|
| 3,992,553 | 11/1976 | Sirrenberg | 564/44 |
| 4,005,223 | 1/1977 | Sirrenberg | 564/44 |
| 4,013,717 | 3/1977 | Wellinger | 564/44 |
| 4,041,177 | 8/1977 | Sirrenberg | 564/44 |
| 4,068,002 | 1/1978 | Sirrenberg | 564/44 |
| 4,508,734 | 4/1985 | Lange | 564/44 |
| 4,529,819 | 7/1985 | Clifford | 564/44 |

FOREIGN PATENT DOCUMENTS

| | | | |
|---|---|---|---|
| 57888 | 8/1982 | European Pat. Off. | 564/44 |
| 74074 | 3/1983 | European Pat. Off. | 564/44 |
| 3500468 | 1/1985 | Fed. Rep. of Germany. | |
| 57-2258 | 1/1982 | Japan. | |
| 57-2259 | 1/1982 | Japan. | |

*Primary Examiner*—Allen J. Robinson

[57] ABSTRACT

Compounds of the general formula

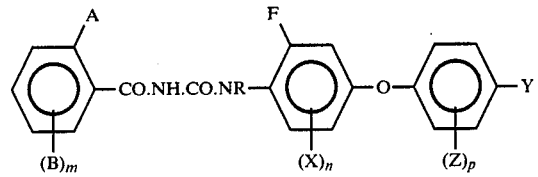

in which each of A and B independently represents a halogen atom or an alkyl group; m is 0 or 1; R represents a hydrogen atom or a group $-S.CO_2R^1$, $-S.SO_2R^1$ or $-S.NR^2R^3$, in which $R^1$ represents an optionally substituted alkyl or aryl group; $R^2$ represents an optionally substituted alkyl or aryl group; and $R^3$ represents an optionally substituted alkyl or aryl group, or a group of formula $-CO_2R^4$, $-SO_2R^4$, $-COR^4$, $-CO.CO_2R^4$, $-CO.NR^5R^6$ or $-SO_2NR^5R^6$, in which $R^4$ represents an optionally substituted alkyl or aryl group, and each of $R^5$ and $R^6$ independently represents an optionally substituted alkyl or aryl group; or $R^2$ and $R^3$ together or $R^5$ and $R^6$ together represent an optionally substituted alkylene group; in each case, the optional substituents for an alkyl or alkylene group being selected from halogen, alkoxy, alkoxycarbonyl, haloalkoxycarbonyl, alkylcarbonyl, haloalkylcarbonyl, alkylsulphonyl and haloalkylsulphonyl, and the optional substituents for an aryl group being selected from these substituents and also alkyl, haloalkyl, cyano and nitro; X represents a halogen atom or a cyano, nitro, alkyl or haloalkyl group; each of Y and Z independently represents a halogen atom or a cyano, nitro or haloalkyl group; n is 0, 1, 2 or 3; and p is 0, 1 or 2; have useful pesticidal activity.

6 Claims, No Drawings

PESTICIDAL BENZOYLUREA COMPOUNDS

This is a division of application Ser. No. 719,791, filed Apr. 4, 1985.

The present invention relates to benzoylurea compounds having pesticidal, especially insecticidal and acaricidal, activity.

UK Patent Specification No. 1,324,293 discloses a class of urea derivatives having insecticidal activity. These compounds are highly active, and include the commercial compound, N-(2,6-difluorobenzoyl)-N'-(4-chlorophenyl)urea. UK Patent Specification No. 1,460,419 discloses similar compounds also having insecticidal properties. The Applicants have now discovered a novel class of urea-type compounds which not only have high insecticidal activity, but also possess acaricidal activity.

The invention provides a compound of the general formula

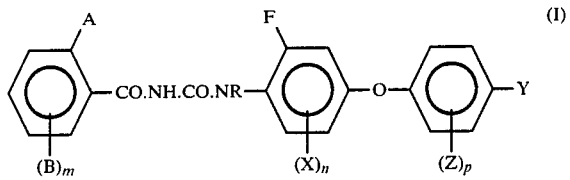 (I)

in which each of A and B independently represents a halogen atom or an alkyl group; m is 0 or 1; R represents a hydrogen atom or a group —S.CO$_2$R$^1$, —S.SO$_2$R$^1$ or —S.NR$^2$R$^3$, in which R$^1$ represents an optionally substituted alkyl or aryl group; R$^2$ represents an optionally substituted alkyl or aryl group; and R$^3$ represents an optionally substituted alkyl or aryl group, or a group of formula —CO$_2$R$^4$, —SO$_2$R$^4$, —COR$^4$, —CO.CO$_2$R$^4$, —CO.NR$^5$R$^6$ or —SO$_2$NR$^5$R$^6$, in which R$^4$ represents an optionally substituted alkyl or aryl group, and each of R$^5$ and R$^6$ independently represents an optionally substituted alkyl or aryl group; or R$^2$ and R$^3$ together or R$^5$ and R$^6$ together represent an optionally substituted alkylene group; in each case, the optional substituents for an alkyl or alkylene group being selected from halogen, alkoxy, alkoxycarbonyl, haloalkoxycarbonyl, alkylcarbonyl, haloalkylcarbonyl, alkylsulphonyl and haloalkylsulphonyl, and the optional substituents for an aryl group being selected from these substituents and also alkyl, haloalkyl, cyano and nitro; X represents a halogen atom or a cyano, nitro, alkyl or haloalkyl group; each of Y and Z independently represents a halogen atom or a cyano, nitro or haloalkyl group; n is 0, 1, 2 or 3; and p is 0, 1 or 2.

Except where otherwise stated, throughout this Specification and claims, any aryl group is preferably a phenyl group. Any alkyl or haloalkyl group preferably has up to 6, especially up to 4, carbon atoms. A preferred alkyl group is methyl, and a preferred haloalkyl group is trifluoromethyl. Any alkylene moiety preferably has 4 to 8 carbon atoms, and is preferably a tetramethylene or pentamethylene group. Halogen atoms may be fluorine, chlorine, bromine or iodine atoms, with fluorine and chlorine being preferred. When n or p is greater than 1, the substituents X or Z present may be the same or different.

Preferably each of A and B independently represents a fluorine or chlorine atom or a methyl group. Most preferably, A is a fluorine atom, m is 1 and B is a fluorine or chlorine atom, preferably in the 6-position of the phenyl ring (A of course being in the 2-position).

Preferably X represents a fluorine or chlorine atom or a methyl group. Thus typically (X)$_n$ may be 3 fluorine atoms, 2 fluorine atoms and a chlorine atom, or a fluorine atom and two chlorine atoms. Most preferably X represents fluorine and n is 3, 2, 1 or, especially, 0.

Preferably Y represents a chlorine atom or a nitro, cyano or trifluoromethyl group. A trifluoromethyl group Y is especially preferred.

Preferably Z represents a chlorine atom or a cyano or nitro group. Preferably p is 0 or 1. Most preferably Z represents a chlorine atom and p is 1; such a chlorine atom is preferably in the position ortho to the oxygen linkage.

When R$^1$, R$^2$, R$^3$, R$^4$, R$^5$ or R$^6$ represents an optionally substituted alkyl group, the alkyl moiety preferably has up to 12, especially up to 6, carbon atoms. Preferably each of R$^1$, R$^4$, R$^5$ and R$^6$, when present, represents an unsubstituted alkyl group having up to 6 carbon atoms.

Preferably R represents a hydrogen atom or a group of formula —S.NR$^2$R$^3$. Preferably R$^2$ represents an unsubstituted alkyl group having up to 6 carbon atoms, especially a methyl group; and preferably R$^3$ represents an alkyl group having up to 6 carbon atoms substituted by an alkoxycarbonyl group having up to 6 carbon atoms in the alkyl moiety, or R$^3$ represents a group of formula —CO$_2$R$^4$, —SO$_2$R$^4$, —COR$^4$, —CO.CO$_2$R$^4$, —CO.NR$^5$R$^6$ or —SO$_2$NR$^5$R$^6$; or R$^2$ and R$^3$ together represent an alkylene group having 4 or 5 carbon atoms and optionally substituted by an alkoxycarbonyl group having up to 6 carbon atoms in the alkyl moiety.

Especially preferred groups R are those of formula —S.NR$^2$CO$_2$R$^4$ in which each of R$^2$ and R$^4$ represents an unsubstituted alkyl group having up to 6 carbon atoms.

Also preferred are compounds of the formula I in which R represents a hydrogen atom.

The invention also provides a process for the preparation of a compound of the general formula I, which comprises reacting a compound of the general formula

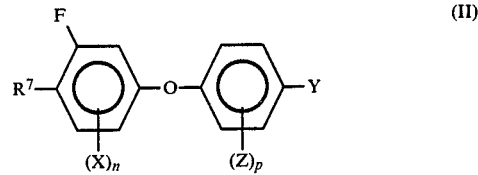 (II)

with a compound of the general formula

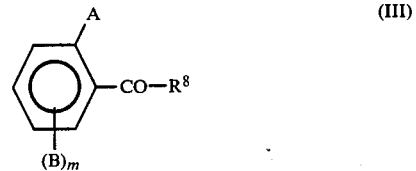 (III)

in which A, B, m, X, Y, Z, n and p have the meanings given for the general formula I, and either R$^7$ represents an —NHR group in which R has the meaning given for the general formula I and R$^8$ represents an —NCO group, or R$^7$ represents an —NCO group and R$^8$ represents an —NH$_2$ group.

The reaction is suitably carried out in the presence of a solvent. Suitable solvents are aromatic solvents such as benzene, toluene, xylene, or chlorobenzene, hydrocarbons such as petroleum fractions, chlorinated hydrocarbons such as chloroform, methylene chloride or dichloroethane, and ethers such as diethyl ether, dibutyl ether, or dioxan. Mixtures of solvents are also suitable.

Preferably the reaction is carried out at a temperature from 0° C. to 100° C., suitably ambient temperature. Preferably the molar ratio of isocyanate to amine is from 1:1 to 2:1. Preferably the reaction is carried out under anhydrous conditions.

The compounds of formula II are themselves novel and constitute a further aspect of the invention; they may be prepared by reacting a compound of the general formula

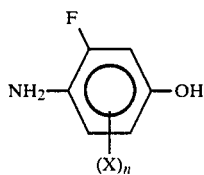

(IV)

with a compound of the general formula

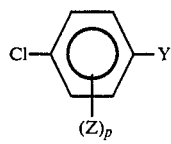

(V)

in which X, n, Y, Z, and p have the meanings given for the general formula II, to produce a compound of the general formula II in which $R^7$ is —$NH_2$; and if desired, reacting said compound with phosgene to produce the corresponding compound in which $R^7$ is —NCO, or with a compound of the general formula HAl—R in which R represents a group —$S.CO_2R^1$, —$S.SO_2R^1$ or —$S.NR^2R^3$, to produce the corresponding compound of the general formula II in which $R^7$ represents a group —NHR and R represents a group —$S.CO_2R^1$, —$S.SO_2R^1$ or —$S.NR^2R^3$.

The reaction between the compounds of formulae IV and V is preferably carried out in the presence of an inert solvent, for example a polar aprotic solvent such as dimethylsulphoxide or dimethylformamide, in the presence of a base, for example an alkali metal hydroxide, alkoxide or carbonate, or an organic base such as pyridine or triethylamine. The reaction temperature is suitably in the range of form 0° to 150° C., preferably 30° to 100° C. The compounds of formula II in which $R^7$ is —NCO may be prepared by the reaction of a compound of formula II where $R^7$ is —$NH_2$ with phosgene. This reaction is suitably carried out in the presence of a solvent, preferably a hydrocarbon or chlorinated hydrocarbon, at a temperature in the range of from 0° to 100° C., room temperature often being convenient. Compounds of formula II in which $R^7$ is —NHR and R is other than hydrogen may be prepared by reacting the corresponding compound of formula II in which R is hydrogen with a compound of the general formula Hal—R in which Hal represents a halogen, especially chlorine, atom. This reaction is preferably carried out in the presence of an inert solvent, for example a hydrocarbon or chlorinated hydrocarbon, and the reaction temperature is preferably in the range of from —30° to +30° C., preferably —10° to +10° C. The reaction is suitably carried out in the presence of a base, for example an amine such as triethylamine.

The compounds of the general formula I exhibit pesticidal, for example insecticidal and acaricidal, activity. Accordingly the invention also provides a pesticidal composition comprising a compound of the general formula I together with a carrier. The invention further provides a method of combating pests at a locus, which comprises applying to the locus a pesticidal compound or composition according to the invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension conentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing pesticidal, herbicidal, or fungicidal properties. The compounds of the invention are especially useful when applied in admixture with other insecticides, especially organophosphates and pyrethroids. Mixtures with the commercial products fenvalerate, permethrin, cypermethrin, deltamethrin and alphamethrin are especially useful.

The following Examples illustrate the invention; Examples 1 to 4 illustrate the preparation of intermediates of the formula II, while Examples 5 to 7 illustrate the preparation of compounds of the formula I.

EXAMPLE 1

Preparation of 2-fluoro-4-(2-chloro-4-[trifluoromethyl]-phenoxy)aniline

A solution of 2-fluoro-4-hydroxyaniline (7.1 g) and potassium hydroxide (3.7 g, 85% pure) in dimethylsulphoxide (25 ml) was heated to 80° C. and treated with a solution of 1,2-dichloro-4-(trifluoromethyl)benzene (10.9 g) in dimethylsulphoxide (10 ml). The mixture was stirred at 90°–95° C. for 20 hours, after which time it was diluted with a mixture of water and dichloromethane. The organic phase was dried over sodium sulphate and evaporated down to give 3.6 g of the crude desired product as a brown oil.

Chromatography over silica gel using toluene/petroleum ether (4:1 ratio) gave 1.1 g of the pure amine as a yellow oil.

Elemental Analysis: Calculated: C; 51.1% H; 2.6% N; 4.6%. Found: C; 50.3% H; 2.7% N; 4.3%.

EXAMPLE 2

Preparation of propyl N-[[[4-[2-chloro-4-(trifluoromethyl)phenoxy]-2-fluorophenyl]amino]thio]-N-methylcarbamate A solution of propyl N-chlorosulphenyl-N-methylcarbamate (12.1g) in diethyl ether (20 ml) was added to a stirred solution of the compound of Example 1 (18.3 g) and triethylamine (7 g) in the same solvent (70 ml) over 20 minutes, the temperature being maintained at 15°–20° C. with cooling. Stirring was continued at room temperature for a further 1½ hours. The reaction mixture was then diluted with diethyl ether (200 ml), washed with water, dried and stripped of solvent. The residue was added to 100 mls toluene, and the toluene was removed under reduced pressure to leave 26.5 g of the desired product in crude form as a brown oil.

EXAMPLE 3

Preparation of N-[[[4-[2-chloro-4-(trifluoromethyl)phenoxy]-2-fluorophenyl]amino]thio]-N-methylbutanamide A solution of sulphur dichloride (11.3 g) in dichloromethane (10 ml) was added over 20 minutes to a solution of N-methylbutanamide (10.1 g) in the same solvent (35 ml) with stirring, the temperature being maintained at 10° C. Stirring at this temperature was continued for a further 30 minutes after which time a solution of pyridine (8.7 g) in dichloromethane (15 ml) was added. The mixture was then stirred and allowed to warm to room temperature over 2 hours, then filtered. The solvent was stripped off and the residue extracted with diethyl ether. After filtration, solvent removal and distillation, 12.1 g of the sulphenyl chloride as an oil, boiling point 82°–84° C. at 13 mmHg, was obtained. 4.4 g of this oil was dissolved in diethyl ether (10 ml) and the resulting solution was added over 20 minutes to a mixture of the compound of Example 1 (7.6 g) and triethylamine (2.7 g) in diethyl ether (30 ml). After stirring for 30 minutes at room temperature, 150 ml diethyl ether was added, the resultant soution was washed three times with water, dried, stripped of solvent and purified by chromatography over silica using dichloromethane as eluant. 9.1 g of the desired product was obtained as a brown oil.

EXAMPLE 4

Preparation of
N-[[[4-[2-chloro-4-(trifluoromethyl)phenoxy]-2-fluorophenyl]amino]thio]-L-proline, methyl ester A solution of sulphur dichloride (11.3 g) in dichloromethane (20 ml) was added at room temperature over 15 minutes to a stirred solution of L-proline, methyl ester hydrochloride (16.6 g) in the same solvent (50 ml), following which a solution of pyridine (17.4 g) in the same solvent (20 ml) was added to the reaction mixture over 30 minutes. After stirring overnight, the mixture was diluted with diethyl ether (150 ml), filtered, and stripped of solvent to leave 17.8 g of the crude product. 4.3 g of this product was dissolved in diethyl ether (10 ml) and added over 15 minutes at room temperature to a stirred mixture of the compound of Example 1 (6.1 g), triethylamine (2.2 g) and diethyl ether (50 ml). After stirring at room temperature for 30 minutes, 250 mls of diethyl ether were added, and the mixture was washed with water, dried and stripped of solvent. After chromatography over silica using a mixture of diethyl ether and petroleum ether as eluant, 6.9 g of the desired crude product was obtained in the form of a brown oil.

EXAMPLE 5

Preparation of
N-(2,6-difluorobenzoyl)-N'-(2-fluoro-4-[2-chloro-4-(trifluoromethyl)phenoxy]phenylurea A solution of the compounds of Example 1 (0.9 g) in dry toluene (5 ml) was treated with 2,6-difluorobenzoylisocyanate (0.56 g) and the mixture was stirred at room temperature overnight. The precipitated product was then separated, washed with cold methanol and dried in an oven at 60° C. 1.15 g of the desired product were obtained, melting point 173°–174° C.

Elemental Analysis: Calculated: C; 51.6% H; 2.3% N; 5.7%. Found: C; 51.7% H; 2.1% N; 5.7%.

EXAMPLE 6

Preparation of propyl
4-[4-[2-chloro-4-(trifluoromethyl)phenoxy]-2-fluorophenyl]-7-(2,6-difluorophenyl)-2-methyl-5,7-dioxo-3-thia-2,4,6-triazaheptanoate A solution of 2,6-difluorobenzoyl isocyanate (2.0 g) in dry methylene chloride (10 ml) was added rapidly to a stirred solution of the compound of Example 2 (4.5 g) in the same solvent (20 ml) at room temperature. After stirring for 4 hours the solvent was removed under reduced pressure, and the residue was purified by chromatography (2x) on silica, using first methylene chloride and then diethyl ether as eluant. The product thus obtained was finally purified by crystallisation from diethyl ether/light petroleum affording colourless crystals (4.5 g) melting at 98°–99° C.

Elemental Analysis Calculated: C; 49.1% H; 3.2% N; 6.6%. Found: C; 49.4% H; 3.1% N; 6.5%.

EXAMPLE 7

Preparation of
N-[[[4-[2-chloro-4-(trifluoromethyl)-phenoxy]-2-fluorophenyl][[(2,6-difluorobenzoyl)amino]carbonyl]amino]thio-N-methylbutanamide A solution of 2,6-difluorobenzoylisocyanate (2.0 g) in a 1:1 mixture of toluene and petroleum ether (5 ml) was added at room temperature over 30 minutes to a stirred solution of the compound of Example 3 (4.4 g) in the same solvent (20 ml). After stirring at room temperature for 2 hours, the solid product was filtered off and recrystallised from a mixture of diethyl ether and petroleum ether to give 4.3 g of the desired product, melting point 136°–138° C.

Elemental Analysis: Calculated: C; 50.4% H; 3.2% N; 6.8%. Found: C; 50.6% H; 3.2% N; 6.6%.

EXAMPLE 8

Preparation of
N-[[[4-[2-chloro-4-(trifluoromethyl)phenoxy]-2-fluorophenyl][[(2,6-difluorobenzoyl)amino]carbonyl]amino]thio-L-proline, methyl ester A solution of 2,6-difluorobenzoylisocyanate (2.8 g) in a 1:1 mixture of toluene and petroleum ether (10 ml) was added at room temperature over 30 minutes to a stirred solution of the compound of Example 4 (6.5 g) in the same solvent (20 ml). After stirring at room temperature for 3 hours, the solvent was stripped and the residue purified by chromatography over silica using dichloromethane as eluant, to give 5.5 g of the desired product, melting point 65°–68° C.

Elemental Analysis: Calculated: C; 50.0% H; 3.1% N; 6.5%. Found: C; 50.2% H; 3.3% N; 6.3%.

EXAMPLES 9 TO 25

By methods analogous to those of Examples 5 to 8, further compounds of the general formula I were prepared from intermediates of the general formula II. Details are given in Table I.

TABLE I

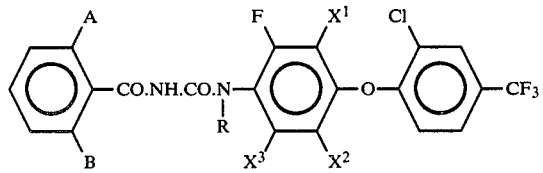

| | | In the formula above | | | | MPt. | | Elemental Analysis | | |
|---|---|---|---|---|---|---|---|---|---|---|
| Example No. | A | B | R | $X^1$ | $X^2$ | $X^3$ | °C. | | C | H | N |
| 9 | F | Cl | H | H | H | H | 153–154 | Calc. | 49.9 | 2.2 | 5.6 |
| | | | | | | | | Found | 50.2 | 2.2 | 5.6 |
| 10 | F | F | H | F | F | F | 196-7 | Calc. | 46.5 | 1.5 | 5.2 |
| | | | | | | | | Found | 46.4 | 1.5 | 5.1 |
| 11 | F | F | H | H | H | F | 203–5 | Calc. | 49.8 | 2.0 | 5.5 |
| | | | | | | | | Found | 49.5 | 2.0 | 5.3 |
| 12 | F | F | H | H | F | H | 199–201 | Calc. | 49.8 | 2.0 | 5.5 |
| | | | | | | | | Found | 50.1 | 1.8 | 5.3 |

TABLE I-continued

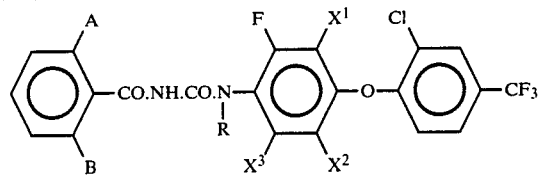

| Example No. | A | B | R | X¹ | X² | X³ | MPt. °C. | | Calc./Found C | H | N |
|---|---|---|---|---|---|---|---|---|---|---|---|
| 13 | F | F | H | F | F | H | 185-6 | Calc. | 48.1 | 1.7 | 5.3 |
| | | | | | | | | Found | 48.1 | 1.6 | 5.0 |
| 14 | F | F | SN($^i$C$_4$H$_9$)CO$_2$C$_2$H$_5$ | H | H | H | 96-98 | Calc. | 50.6 | 3.6 | 6.3 |
| | | | | | | | | Found | 50.9 | 4.0 | 6.1 |
| 15 | F | F | SN(CH$_3$)CO$_2$$^i$C$_3$H$_7$ | H | H | H | 82-85 | Calc. | 49.1 | 3.1 | 6.6 |
| | | | | | | | | Found | 49.0 | 2.9 | 6.4 |
| 16 | F | F | SN($^n$C$_4$H$_9$)CO$_2$Me | H | H | H | 116-118 | Calc. | 49.9 | 3.4 | 6.5 |
| | | | | | | | | Found | 49.7 | 3.3 | 6.2 |
| 17 | F | F | SN(CH$_3$)CO$_2$$^i$C$_4$H$_9$ | H | H | H | 115-117 | Calc. | 49.9 | 3.4 | 6.5 |
| | | | | | | | | Found | 50.7 | 3.5 | 6.3 |
| 18 | F | F | SN($^i$C$_3$H$_7$)CO$_2$CH$_3$ | H | H | H | 99-101 | Calc. | 49.1 | 3.2 | 6.6 |
| | | | | | | | | Found | 49.0 | 3.0 | 6.9 |
| 19 | F | F | SN($^i$C$_3$H$_7$)CO$_2$$^n$C$_3$H$_7$ | H | H | H | 116-118 | Calc. | 50.6 | 3.6 | 6.3 |
| | | | | | | | | Found | 51.1 | 3.6 | 6.5 |
| 20 | F | F | SN(CH$_3$)CO$_2$$^n$C$_4$H$_9$ | H | H | H | 72-75 | Calc. | 49.9 | 3.4 | 6.5 |
| | | | | | | | | Found | 50.1 | 3.3 | 6.3 |
| 21 | F | F | SN(CH$_3$)CO$_2$$^n$C$_{10}$H$_{21}$ | H | H | H | gum | Calc. | 54.0 | 4.6 | 5.7 |
| | | | | | | | | Found | 54.1 | 5.1 | 5.5 |
| 22 | F | F | SN(CH$_3$)COCH$_3$ | H | H | H | 107-110 | Calc. | 48.7 | 2.7 | 7.1 |
| | | | | | | | | Found | 48.8 | 2.4 | 6.9 |
| 23 | F | F | SN(CH$_3$)CO$^n$C$_5$H$_{11}$ | H | H | H | 116-118 | Calc. | 51.9 | 3.7 | 6.5 |
| | | | | | | | | Found | 52.0 | 3.9 | 6.4 |
| 24 | F | F | SN(CH$_3$)CO$^i$C$_4$H$_9$ | H | H | H | 94-96 | Calc. | 51.1 | 3.5 | 6.6 |
| | | | | | | | | Found | 51.4 | 3.7 | 6.2 |
| 25 | F | F | SN(CH$_3$)CO$^n$C$_{11}$H$_{23}$ | H | H | H | 62-65 | Calc. | 55.8 | 4.9 | 5.7 |
| | | | | | | | | Found | 55.7 | 5.0 | 5.5 |

EXAMPLE 26

Insecticidal Activity

The insecticidal activity of the compounds of the invention was determined in the following tests, employing the insects *Spodoptera littoralis* (S.1.) and *Aedes aegypti* (A.a)

The test methods used for each species appear below. In each case the tests was conducted under normal conditions (23° C.±2° C.; fluctuating light and humidity).

In each test an LC$_{50}$ (the dosage of active material required to kill half of the test species) for the compound was calculated from the mortality figures and compared with the corresponding LC$_{50}$ for a standard insecticide, ethyl parathion, in the same tests. The results are expressed as toxicity indices thus:

$$\text{toxicity index} = \frac{LC_{50} \text{ (parathion)}}{LC_{50} \text{ (test compound)}} \times 100$$

and are set out in Table III below.

(i) *Spodoptera Littoralis*

Solutions or suspensions of the compound were made up over a range of concentrations in 10% acetone/water containing 0.025% Triton X100 ("Triton" is a registered trade mark). These solutions were sprayed using a logarithmic spraying machine onto petri dishes containing a nutritious diet on which the *Spodoptera littoralis* larvae had been reared. When the spray deposit had dried each dish was infested with 10 2nd instar larvae. Mortality assessments were made 7 days after spraying.

(ii) *Aedes aegypti*

Several solutions of the test compound of varying concentration were prepared in acetone. 100 microliter quantities were added to 100 ml of tap water, the acetone being allowed to evaporate off. 10 early 4th instar larvae were placed in the test solution; after 48 hours the (surviving) larvae were fed with animal feed pellets, and the final percentage mortality assessed when all the larvae had either pupated and emerged as adults or died. The results are given in Table II.

TABLE II

Insecticidal Activity

| Compound of Example No. | Toxicity Index | |
|---|---|---|
| | S.1. | A.a. |
| 5 | 5600 | 1300 |
| 6 | 2800 | 790 |
| 7 | 1500 | 800 |
| 8 | 2700 | Not tested |
| 9 | 5300 | 960 |
| 10 | 180 | 180 |
| 11 | 1630 | 260 |
| 12 | 9500 | 380 |
| 13 | 3500 | Not tested |
| 14 | 5500 | 620 |
| 15 | 5200 | 1290 |
| 16 | 6300 | 810 |
| 17 | 3000 | 950 |
| 18 | 6230 | 1370 |
| 19 | 4360 | 940 |
| 20 | 1840 | 1500 |
| 21 | 2800 | 1100 |
| 22 | 2000 | 470 |
| 23 | 2100 | 530 |
| 24 | 3700 | Not tested |
| 25 | 2000 | Not tested |

EXAMPLE 27

Acaricidal Activity

Leaf discs were infested with 30–60 larvae of the mite *Tetranicus urticae* and sprayed with varying dosages of solutions of the test compound made up as in test (i) of Example 26 above. When dry, the discs were maintained at constant temperature for 12 days, after which mortality assessments were made, and the $LC_{50}$ values calculated. Also included in the test were two compounds of UK Pat. No. 1,460,419 of very closely related structure, given below, and the commercial compound N-(2,6-difluorobenzoyl)-N'-(4-chlorophenyl)urea, of UK Specification No. 1,324,293. The results are given in Table III below. The results show that the compounds of the invention exhibit considerably greater activity than the two prior art compounds.

Comparison Compounds:

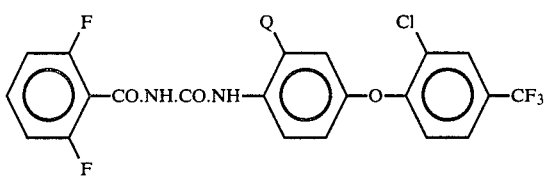

Comparison Compound A: Q=CH$_3$
Comparison Compound B: Q=Cl
Comparison Compound C: N-(2,6-difluorobenzoyl)-N'-(4-chlorophenyl)urea

TABLE III

| Compound of Example No. | Acaricidal Activity LC$_{50}$ (% active ingredient in spray) |
|---|---|
| 5 | 0.00013 |
| 6 | 0.00025 |
| 7 | 0.00015 |
| 8 | Not tested |
| 9 | 0.00025 |
| 10 | 0.00030 |
| 11 | 0.00015 |
| 12 | Not tested |
| 13 | Not tested |
| 14 | 0.00038 |
| 15 | 0.00028 |
| 16 | 0.00021 |
| 17 | 0.00028 |
| 18 | 0.00018 |
| 19 | 0.00029 |
| 20 | 0.00015 |
| 21 | Not tested |
| 22 | Not tested |
| 23 | Not tested |
| 24 | 0.00010 |
| 25 | Not tested |
| Comparison Compounds A | 0.0032 |
| B | 0.00069 |
| C | >0.1% |

I claim:

1. A method for controlling insecticidal and acaricidal pests at a locus that comprises applying to the locus an effective dosage of a compound of the formula

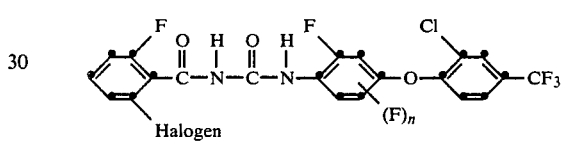

in which "halogen" represents chlorine or fluorine and n is zero, one, two or three.

2. A method according to claim 1 wherein "halogen" is fluorine.

3. A method according to claim 2 wherein n is zero.

4. A method according to claim 1 wherein the pest is an acarid.

5. A method according to claim 2 wherein the pest is an acarid.

6. A method according to claim 3 wherein the pest is an acarid.

* * * * *